United States Patent [19]

Tobi

[11] Patent Number: 5,244,801
[45] Date of Patent: Sep. 14, 1993

[54] PROCESS FOR PRODUCING MONOCLONAL ANTIBODIES WHICH SPECIFICALLY BIND TO BENIGN COLONIC ADENOMATOUS POLYPS OF HUMAN ORIGIN AND HYBRIDOMAS AND MONOCLONAL ANTIBODIES PRODUCED BY SAID PROCESS

[76] Inventor: Martin Tobi, 26715 W. Carnegie Park Dr., Southfield, Mich. 48034

[21] Appl. No.: 458,498

[22] Filed: Dec. 28, 1989

[51] Int. Cl.$^5$ .................. C12N 5/20; C12N 15/02; C12P 21/08; C07K 15/28

[52] U.S. Cl. .................. 435/240.27; 435/172.2; 435/70.21; 530/388.85; 530/388.8; 530/387.7

[58] Field of Search ............... 530/387, 388.85, 388.8, 530/387.7; 435/240.27, 70.21, 172.2

[56] References Cited

U.S. PATENT DOCUMENTS

| | | | |
|---|---|---|---|
| 4,172,124 | 10/1979 | Koprowski | 424/85.8 |
| 4,349,528 | 9/1982 | Koprowski | 424/388.85 |
| 4,522,918 | 6/1985 | Schlom et al. | 435/70.21 |
| 4,892,933 | 1/1990 | Salem et al. | 530/388.85 |
| 4,921,789 | 5/1990 | Salem et al. | 435/7.23 |

OTHER PUBLICATIONS

Brown et al. Bioscience Reports 3:163-170, 1983.
Raffaella Muraro et al., "Generation of Monoclonal Antibodies Reactive With Human Colon Carcinomas" Genetic and Phenotypic Marks of Tumors, pp. 117-127 (1985).
S. K. Khoo et al., "Carcinoembryonic Antigenic Activity of Tissue Extracts: A Quantitative Study of Malignant and Benign Neoplasms, Cirrhotic Lever, Normal Adult and Fetal Organs" Int. J. Cancer: 11, pp. 681-687 (1973).
Advanced Concepts in Cancer Research, Israel Cancer Research Fund, Program and Abstracts, Mar. 6-10, 1988 p. 60, Tobi et al.
Annual Meeting of the Cancer Biology Research Center, Cancer Biology Research Center, Jan. 26-28, 1989, p. 49, Tobi et al.
Scientific Meetings in Israel, vol. 25, No. 3, Mar. 1989, pp. 175 and 176, Israel Journal of Medical Science 25(3), Tobi et al.

Primary Examiner—David L. Lacey
Assistant Examiner—Paula Hutzell
Attorney, Agent, or Firm—Oblon, Spivak, McClelland, Maier & Neustadt

[57] ABSTRACT

Monoclonal antibodies manifesting specific reactivity to benign adenomatous polyps of the human colon are produced. Hybridoma technology was utilized to produce immunoglobulin producing cell lines. Splenic lymphocytes from mice, immunized with a membrane fraction derived from human tubular adenomatous colonic polyps, were fused with a mouse non immunoglobulin secreting myeloma cell line (NS-1). Screening of hybridoma culture supernatant for positive reactivity with adenomatous colonic polyp extract, and negative activity with extracts from normal liver and spleen allowed for selection of desired immunoglobulin producing cultures. Further screening of expanded cultures with extracts of colorectal cancer, apparently normal mucosa adjacent to the cancer, and a variety of normal human extracts allowed further distinctions in binding reactivity. One such selected cell line produced a monoclonal antibody designated Adnab-9 selected on this basis. Adnab-9 was reacted with colonic-washing effluent derived from patients undergoing routine precolonoscopic bowel cleansing and the resultant mean binding activity in the effluent of patients proved to have a colorectal cancer was significantly elevated with respect to those with an apparently normal colon. Since Adnab-9 binding may be increased in some colorectal cancer patients with early stage disease, Adnab-9 aids in the diagnosis, and timely treatment of colorectal cancer.

10 Claims, 2 Drawing Sheets

PROCESS FOR PRODUCING MONOCLONAL ANTIBODIES WHICH SPECIFICALLY BIND TO BENIGN COLONIC ADENOMATOUS POLYPS OF HUMAN ORIGIN AND HYBRIDOMAS AND MONOCLONAL ANTIBODIES PRODUCED BY SAID PROCESS

BACKGROUND OF THE INVENTION

The invention described herein was, in part, made in the course of work performed at the National Institutes of Health of the U.S. Department of Health and Human Services.

FIELD OF THE INVENTION

The present invention is related to the production of monoclonal antibodies reactive with colonic polyps and use of these antibodies in the diagnosis of colorectal cancer.

DISCUSSION OF THE BACKGROUND

Hybridoma technology as developed by Kohler and Milstein is well established as a method of producing antibodies of pre-determined specificity (Kohler G. and Milstein C., 1975, Nature (London), 256, 494–497. See, for example, U.S. Pat. Nos. 4,172,124, 4,196,265 and 4,522,918 which teach monoclonal antibody production by hybridoma techniques. Solid phase radioimmunoassay (Colcher et al, 1981, Cancer Research 41, 1451–1459) and enzyme linked immunosorbent assay (Methods in Enzymology (73); Immunochemical Techniques, Pt B, pp. 471–550 London, Academic Press, (1981) Phillips and Lewis, Aust. N. Z.. Journal of Surgery 48(5), 545–549, October 1978).

Background art regarding monoclonal antibodies and reactivity in colonic effluent material is outlined in Tobi et al, Gastroenterology, May 1987, Vol. 92 No. 5, p 1672 and Tobi et al, Gastroenterology, December 1988, Vol. 95, pp. 1693–1694. Current non-invasive screening for colorectal cancer in an average risk population involves the detection of occult blood in the stools, a technique that has been found lacking in Simon, 1985, Gastroenterology, 88, 820–837.

Detection of tumor antigens such as carcinoembryonic antigen (CEA) in blood and/or colonic lavage has not been diagnostic for colorectal cancer at all locations when using polyclonal antibodies and physico-chemical methods as discussed in Winawer et al, Gastroenterology, 1977, Vol. 73, pp. 719–722, and Vellacott et al, Clinical Oncology, 1982, Vol. 8, pp. 61–67. Detection of CEA in feces may aid in diagnosis as discussed in Freed et al, British Medical Journal, 1972, Vol. 1, pp 85–87; Elias et al, Diseases of the Colon and Rectum, 1974, Vol. 17, pp 38–41; Stubbs et al, 1986, Vol. 27, pp 901–905.

Diagnosis of early neoplastic change in the human colon might be enhanced by detection of an early tumor marker found on benign adenomatous colon polyps, which would be a distinct departure from the conventional approach. However, immunization of mice with colonic adenoma tissue yielded a monoclonal antibody reactive with a blood group substance (BGA) found in colorectal cancers (Brown et al, Bioscience Reports, 1983, Vol. 3, pp 163–170).

A need continues to exist for a method of producing antibodies reactive with human colonic tissue and for a method of detecting and diagnosing colorectal cancer.

SUMMARY OF THE INVENTION

Accordingly, one object of this invention to produce monoclonal antibodies maximally reactive with human colonic adenomatous tissue, use of the antibodies to recognize a putative early tumor antigen associated with colorectal cancer in the colonic-washing effluent, and a method to diagnose the presence of this disease.

This and other objects which will become apparent Following specification have been achieved by from the the present monoclonal antibodies, processes for producing the antibodies and methods of detecting colorectal cancer using the antibodies.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
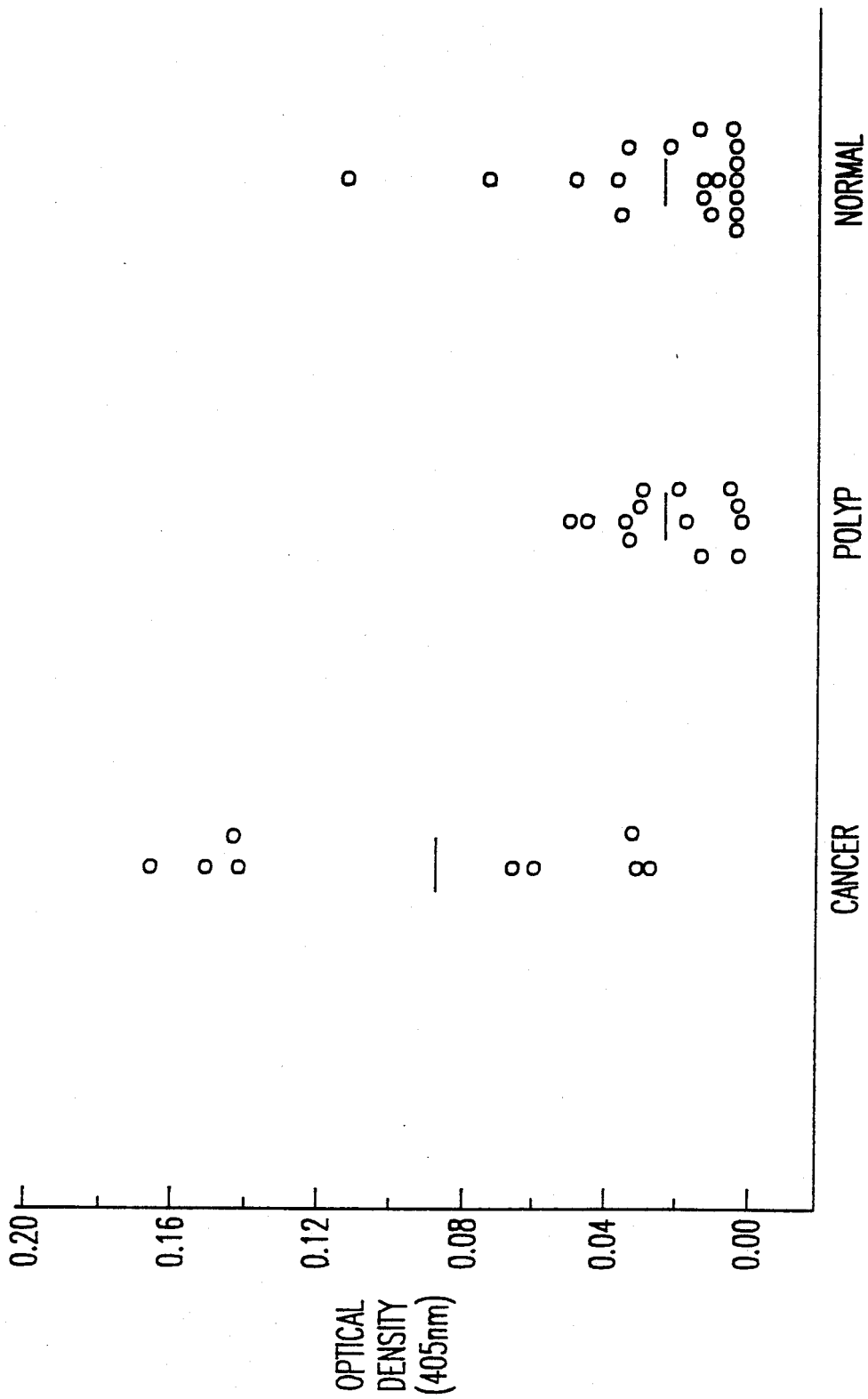
FIG. 1 shows reactivity of binding of Adnab-9 antibodies to colonic effluent from 3 different pathology categories at 5 ug of protein per well in a solid-phase enzyme-linked immunosorbent assay. The short horizontal lines denote the mean values.

As a result of vigorous research aimed at obtaining monoclonal antibodies reactive with human adenomatous tissue, the present inventor has succeeded in producing monoclonal antibodies by a method involving fusion of mouse myeloma cells and mouse splenocytes to produce a hybridoma which produces monoclonal antibodies useful in the detection and diagnosis of human colorectal cancer. The present invention is, therefore, directed to murine monoclonal antibodies which are specific for human adenomatous polyp tissue, but relatively non-reactive against extracts of normal human liver and spleen as well as colorectal cancer cells. In addition, the invention is directed to hybridomas which produce such murine monoclona antibodies which are formed by the fusion of murine splenocytes and murine myeloma cells. Hybridoma Adnab-9 was deposited on Dec. 20, 1989 at the American Tissue Culture Collection (ATCC) 12301 Parklawn Drive, Rockville, Md. and has been assigned the accession number HB10313.

Another aspect of this invention is a method for the screening of a general population for colorectal cancer using the monoclonal antibodies of the present invention. Since the monoclonal antibodies are selectively reactive against human adenomatous polyp tissue but are non-reactive with normal human tissue, the antibodies may be used to identify and diagnose the presence of colorectal cancer in early stages of the disease by screening colonic effluent material.

In the present method, splenocytes are obtained by immunizing mice with the membranes from adenomatous polyps of the colon or an extract thereof and obtaining splenocytes from the spleens of the immunized mice. Preferably, the adenomatous polyp membranes are homogenized, other cell fragments are removed and the cell extract pooled to form a membrane enriched extract which is injected into suitable mice with or without adjuvant. The mice are then sacrificed, their spleens are removed, and a spenocyte cell suspension is prepared.

The spenocytes are then fused with non-immunoglobulin secreting mouse myeloma cells to generate primary hybridoma cultures. Immunoglobulins secreted by the primary hybridoma cultures are screened by solid phase radioimmunoassay for maximal reactivity against pooled human adenomatous polyp extract and for non-reactivity against extracts of normal human liver and spleen extracts. Selected hybridoma cultures producing antibodies of the desired reactivity are then cloned, further screened as above, and those retaining the desired reactivity are screened once more. In addition, the cultures are screened for minimal reactivity with extract antigens such as carcinoembryonic antigen, blood group antigens and colonic effluent from patients with a macroscopically normal colon as determined by colonoscopy.

The cloned progeny are then selected for cancer detecting ability by reacting the antibodies produced by the hybridomas with colonic effluent of patients having colorectal cancer, benign polyps, and a colonoscopically normal colonic mucosa. The binding activity of the antibody to colorectal cancer cell lines is assessed by enzyme-linked immunosorbent assay (ELISA).

Splenocytes which may be used in the present invention include any splenocyte isolated from the spleen of mice which have been immunized (primed) with tissue obtained from human adenomatous polyps of the colon. Tissue extracts for immunizing mice may include all morphological human adenomatous polyps, such as tubular, tubulovillous and villous adenomatous polyps. Extracts for mouse immunization are prepared from the polyp tissue by homogenizing the tissue under conditions which disrupt the cells and then centrifuging the homogenize tissue to remove cell fragments. Proteins isolated from the supernatent are injected into selected mice in an adjuvant or saline solution to achieve immunization.

As the mouse myeloma cells, it is advantageous to use non-secreting mouse myeloma cells such as an NS-1 BALB/c mouse myeloma cell line, which can be obtained, for example, from the Laboratory of Tumor Immunology and Biology at the National Institute of Health (NIH), Bethesda, MD or ATCC. However, any non-secreting myeloma cells capable of fusing with the sphenocytes may be used. Examples of known BALB/c cell lines include: P3x65Ag8, P3-NS1/1-Ag4-1 (ATCC #TIB-18), SP-1, P3xAgU1, SP2/OAg14 and P3xAg8.6.5.3.

In the present method, hybridomas are prepared using the basic principles described by Kohler and Milstein. The general conditions for cell fusion and the culture of hybridomas is, therefore, known, but have been modified by the inventor to obtain the specific combination of conditions required to enhance formation and propagation of the hybridomas of the present invention.

The preferred conditions were determined to be as follows. Splenocytes and mouse myeloma cells are mixed at a ratio of about 10:1 to 1:10, preferably about 1. A suitable solution for cell fusion, such as RPMI-1640 medium contains about 50 wt. % (75 wt. %) polyethylene glycol 1430-1570 at 37° C. The resulting cell suspension is then added to a 96-well sterile tissue culture plate at a cell density of about 0.5-5 million, preferably about 1 million cells per 100 ul per well. Hybridoma cells are selected by growth in RPMI-1640 medium containing 15% fetal calf serum (heat inactivated) and further containing HAT (hypoxanthineaminopterinthymidine) medium. This medium will only support the growth of the fused cells.

The supernatant of each well is screened and only hybridoma which produce the desired antibodies are selected. Cells of the selected hybridomas are collected, cloning is performed by the limiting dilution method and subclones which stably produce the desired monoclonal antibodies are established.

The hybridomas are then further investigated by analyzing the antigens recognized by the monoclonal antibodies produced by the hybridomas and by investigating the ability of the monoclonal antibodies produced to bind to adenomatous polyp tissue. Hybridomas which produce monoclonal antibodies which bind to adenomatous polyp tissue and have minimal reactivity with carcinoembryonic antigen, blood group antigens and the colonic effluent from patients with macroscopically normal colon tissue are finally selected.

It is significant and surprising that the antibodies produced by the hybridomas of the present invention are specific for human adenomatous polyp tissue but are essentially non-reactive with human blood group antigens. Prior attempts to produce monoclonal antibodies for use in the diagnosis of colorectal cancer have suffered from the limitation of being reactive with blood group substances. In contrast, the antibodies of the present invention are substantially free from interferring reaction with blood group antigens. The antibodies of the present invention have been classified as IgG2-Kappa-type antibodies. It is known that antibodies of IgG22 are directly cytotoxic. Such antibodies may be used to directly destroy adenoma cells. It is believed, therefore, that the antibodies of the present invention may also be directly cytotoxic and therefore useful in destroying adenoma cells.

Using the hybridoma method described above, hybridomas were prepared and the monoclonal antibodies were tested as follows. The solid phase radioimmunoassay screening process using pooled adenomatous polyp extract as the positive and normal liver and spleen as the negative selection criteria, delineated 10 parent cell lines of somatic hybrid cells as potentially useful. Further screening of expanded colonies positively selected out hybridoma colonies with differing reactivity for colorectal cancer, adjacent apparently normal mucosa, and effluent from a patient with a normal colonscopic examination. All supernatants were negative for CEA, blood group antigens (BGA), and colorectal cancer cell line LS-174/T, except slight binding of LS-174/T cell line (+) for the IVA-H5 group. The resultant activities are shown in Table 1.

TABLE 1

| HYBRIDOMA | ADENOMA | CANCER | NORMAL EFFLUENT |
|---|---|---|---|
| VA-E4/A2.A1 | +++ | 0 | 0 |
| /A6.A3 | +++ | 0 | 0 |
| A5 | +++ | 0 | 0 |
| VA-A3/B6.B11 | +++ | 0 | + |
| .D3 | +++ | 0 | + |
| /A7.A4 | +++ | 0 | 0 |
| .A1 | +++ | 0 | 0 |

TABLE 1-continued

| HYBRIDOMA | ADENOMA | CANCER | NORMAL EFFLUENT |
|---|---|---|---|
| .D6 (Adnab-9) | +++ | 0 | 0 |
| IVA-B3/B7.B4 | +++ | +++ | 0 |
| .H12 | +++ | +++ | 0 |
| IA-G10/A2.A8 | +++ | + | + |
| .A11 | +++ | + | + |
| /B3.C1 | + | 0 | 0 |
| IIA-E2/A12.C7 | + | + | 0 |
| .F10 | + | + | 0 |
| /B11.G5 | + | + | 0 |
| /A9.D4 | + | + | 0 |
| IA-E9/B9.A4 | +++ | + | ++ |
| .B6 | +++ | + | + |
| /C1.B4 | ++ | + | + |
| .D12 | ++ | + | + |
| /C9.E8 | +++ | + | ++ |
| IIIA-H7/C5.C1 | ++ | 0 | 0 |
| .C2 | ++ | 0 | 0 |
| /B11.B5 | +++ | 0 | 0 |
| .B9 | ++ | + | 0 |
| IVA-H5/A8.B1 | +++ | ++ | +++ |
| .C8 | +++ | ++ | +++ |
| /B11.F12 | +++ | ++ | +++ |
| .G4 | +++ | ++ | +++ |
| IIIA-E5/B6.B3 | ++ | + | 0 |
| .D9 | ++ | + | 0 |
| /B7.B7 | ++ | + | 0 |
| /A11.E9 | ++ | + | 0 |
| .C4 | ++ | + | 0 |
| VA-D2/A8.A9 | + | 0 | 0 |
| .A10 | + | 0 | 0 |

Solid phase radioimmunoassay results (cpm=counts per minute) are expressed as: <500 cpm=0; 500–2,000 cpm=+; 2,000–5,000=++; >5,000=+++. Enzyme-linked immunosorbent assay results for Adnab-9, as derived from Table 2 is presented here as O.D. (optical density) <0.10=0; 0.10–0.140=+; 0.140–0.40=++; and >0.4=+++.

Adnab-9 reactivity is presented in detail in Table 2. The reactivity is maximal for the tubulovillous adenoma extract and minimal for epithelium adjacent to a colorectal cancer, and an extract from the cancer. Reactivity with extracts of various cell lines are essentially negative.

TABLE 2

Adnab-9 Extract Reactivity

| EXTRACT | O.D./at 405 nm. |
|---|---|
| Tissues: | |
| Adenoma | 0.447 |
| Cancer | 0.100 |
| Mucosa within 5 cm of cancer | 0.122 |
| Cell Lines: | |
| LS-174/T | 0.010 |
| HCT-15 | 0.008 |
| HT-29 | 0.062 |
| Oncofetal and Blood Group Antigens: | |
| Carcinoembryonic antigen | 0.002 |
| Red blood cell membranes* | 0.015 |
| Organ specific neoantigen | 0.040 |

*From a donor pool with ABO, Rh, MNS, P, Kell, Duffy, Kidd, Lewis and Lutheran blood groups.

The differential reactivity of Adnab-9 suggests that this monoclonal antibody recognizes a putative early tumor marker associated with adenomatous polyps of the colon and should allow for diagnosis of colorectal cancer at an early stage. FIG. 1 shows that the mean binding value of Adnab-9 for aqueous colonic effluent from colorectal cancer patients is significantly different from the mean of those derived from the normal group ($p<0.01$), by Students T-test. Of the 3 cases below the arbitrary cutoff of O.D.=0.040, all had early stage disease (Dukes A), and had cancer arising in a pre-existing colonic adenoma. Overall, where the staging of the cancer was known, 5 of 8 patients had Dukes A staging. Of the 3 patients with apparently normal colonoscopic examinations above this level, the one with the highest value had a family history of colorectal cancer, and the remaining two had abnormal findings on barium enema and proctoscopy which necessitated the colonoscopic examinations, which proved negative.

Since pre-colonoscopic bowel preparation by the above regimen has been largely superceded by a balanced electrolyte solution (PES) containing polyethylene glycol 3350 (PEG) as the osmo-active ingredient (Dipalma et al, Gastroenterology 86, 856–860, 1984), the effect of PES on the ELISA was investigated. For comparison, effluent samples were diluted in PBS and in PES and serial dilutions beginning at 10 ug protein per well were reacted with BAC 18.1 to assess the effect of the PES on ELISA outcome. In addition $^{125}$I-labelled organ specific neoantigen (OSN) was incubated in various dilutions of PEG in wells of a polyvinyl 96-well microtiter plate for 24 hours, washed and the wells cut from the plate, and counted in a gammacounter to assess the effect of PEG on the sticking of OSN protein to the plate. The results are described below.

Figure 2:
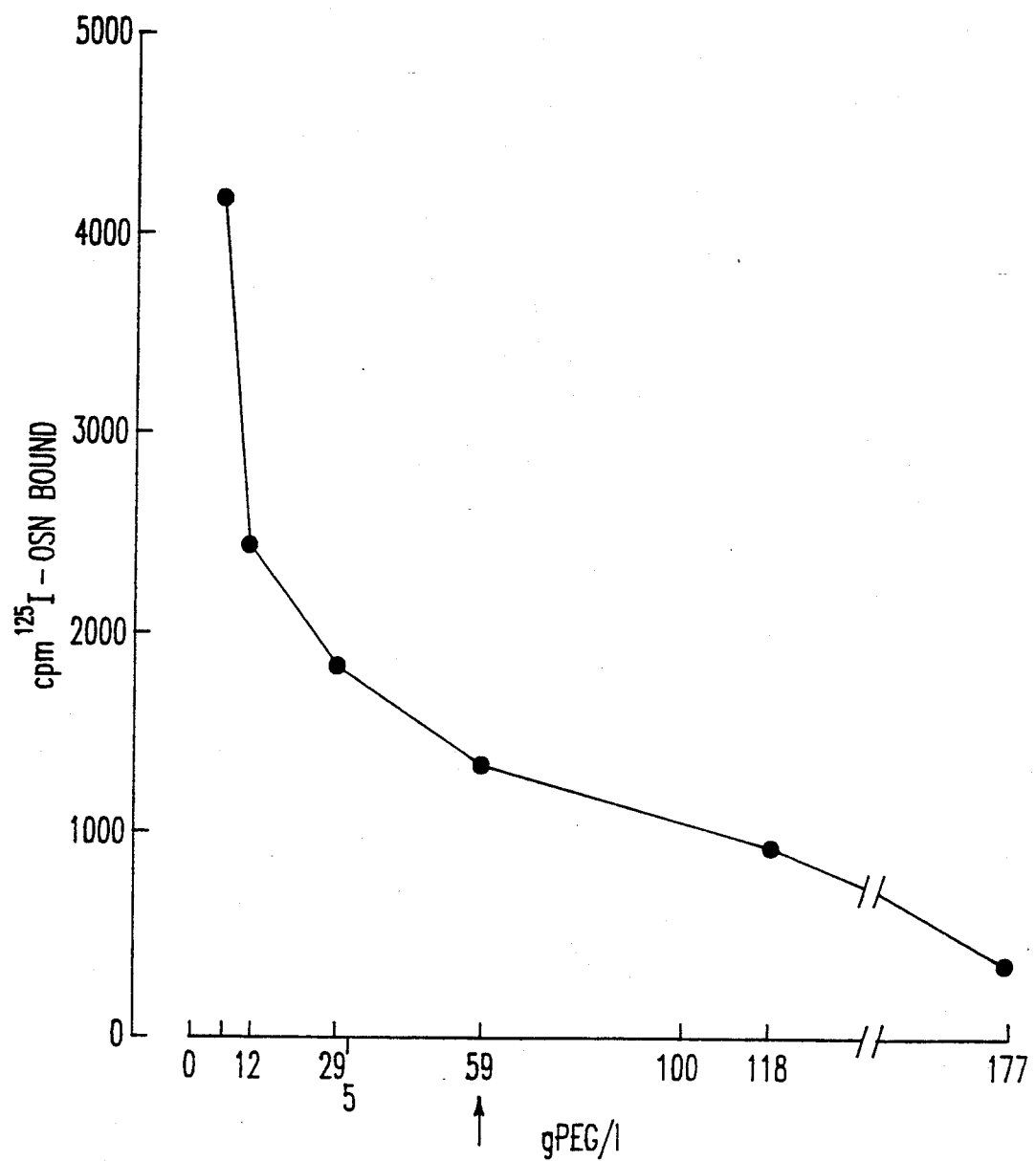
FIG. 2 demonstrates the effect of concentration of polyethylene glycol on the binding of $^{125}I$ labelled organ specific neoantigen to the wells of a plastic microtiter plate. The arrow designates the concentration in most commercially available bowel lavage preparations.

Effluent samples from patients diluted in polyethylene glycol containing balanced electrolyte solutions and reacted in an ELISA with BAC 18.1, were depressed by approximately 50% with respect to the same samples diluted in phosphate-buffered saline (PBS). FIG. 2 shows that polyethylene glycol, at concentrations used in such oral lavage preparations for pre-colonoscopic bowel preparation adversely affects the binding of proteins to polyvinyl plates and explains why such preparations should not be used in conjunction with an ELISA that relies on sticking of an antigen to a plastic plate. Other balanced electrolyte solutions which may be used are disclosed in Rozen et al, Acta Cytologica, in press.

Monoclonal antibodies raised against adenomatous polyps of the colon should be be useful in the major area of colorectal cancer where no effective screening tool is currently available, and where, despite technological advances, the mortality has remained unchanged for the past 40 years. By detecting higher reactivity of a putative early tumor associated antigen shed from the cancer bearing colon, than from the normal colon in laxative-purge/tap water enema effluent samples, the present antibodies, and particularly Adnab-9 will aid in the diagnosis of colorectal cancer, even in the presence of early disease where symptoms of this initially silent disease may not be evident.

The monoclonal antibodies of the present invention may be used to diagnose colorectal cancer as described below. Monoclonal antibodies produced and collected from the hybridomas of the present invention are prepared for use in standard enzyme-linked immunosorbent assay. The preferred antibody is Adnab-9. A human subject is prepared by first undergoing a liquid diet for several days, preferably about 1.5 days with ingestion of bisacodyl, (i.e., (di-4-[(4-4')pyridyl methylene]-diphenol diacetate, tablets and magnesium citrate to purge the colorectal region. On the day of diagnosis, a water enema is administered. The first clear return is discarded. The second return clarified by centrifugation (for example 1500 rpm for 10 minutes) and the protein content is determined by the Lowry method. The exact determination of effluent volume is unnecessary since activity is internally related to protein content.

A standard enzyme-linked immunosorbent assay with the enzyme of the present invention is then performed with the final resulting expressed as O.D./5 ug protein of the effluent sample read at 1-3 hours. The final result is the measurement of binding of the antibody minus the background measurement where antibody-free medium such as PBS or RPMI-1640 medium is substituted for the antibody.

Binding levels of the antibody above the O.D.=0.040 level are suggestive of the presence of colorectal cancer and may be used to diagnose the disease. Improved correlation of antibody binding with disease is obtained by using an arbitrary binding threshhold value, for example O.D.=0.040 as shown in FIG. 1. The present method provides a correlation with the presence of colorectal cancer in about 70% of subjects screened. This diagnosis method is simple and can be performed by laboratory technicians without the need for sophisticated and expensive analytic procedures. The method also enables the screening of large number of persons for colorectal cancer in a timely manner.

Other features of the invention will become apparent in the course of the following descriptions of exemplary embodiments which are given for illustration of the invention and are not intended to be limiting thereof.

EXAMPLE

Tissue and Cell Extracts

Tissue extract for immunization was made from the peripheral shavings of pooled human tubular adenomatous polyps confirmed by histological examination of sections of colonoscopically removed polyps. This tissue was finely minced and homogenized in a hand-held glass pestle and mortar homogenizer for 2 minutes on ice in 0.01M Tris-HCl (pH 7.2), and 0.2 mM calcium chloride. Nitrogen cavitation was achieved by subjection of the homogenate to 1,000 psi of nitrogen for 5 minutes in a cell disruption bomb (Parr Instrument Co., Moline, Ill.), and thereafter centrifuged in a refrigerated laboratory centrifuge at 1,000 Xg for 5 minutes.

The supernatant was fractionated on a discontinuous 20%/40% (10 ml of each concentration) sucrose gradient and ultracentrifuged at 76,000 Xg for 17 hours. Aspiration of the material from the interface, suspension in 0.01M Tris-HCl, and pelleting the same at 76,000 Xg for 1 hour in a SW-27 rotor, yielded a membrane enriched extract. The pellet was resuspended in phosphate buffered saline (PBS) pH 7.2, and a protein estimation was performed by the method of Lowry et al, Journal of Biological Chemistry 193, 265275, 1951.

Tissue extracts for screening were similarly made from pooled tubulovillous polyp fragments, surgically resected colorectal cancer specimens, and the adjacent, apparently normal mucosa. Cell extracts were made from established colorectal cell lines LS174/T (Rutzky et al, Journal of the National Cancer Institute, 63, 893902, 1979); HT-29, Dr. I. Witz, Askinazi Cancer Institute, Tel Aviv; HCT-15 Dr. Z. Bentwich, Ben Ari Institute for Immunology, Rehovot Israel. After the first centrifugation as described above, the supernatants of these tissues were sonicated on ice for 30 seconds at 15 second intervals on a Branson Sonifier at setting 7. The sonicate was further centrifuged at 10,000 Xg and the supernatant constituted a membrane enriched extract as described in Muraro et al, in Genetic and Phenotypic Markers of Tumors pp 117-127, Eds: Aaronson, Frati and Verna, Plenum Press, 1985.

Immunizations

Five four week old BALB/c mice were given 2×100 ug protein intraperitoneal injections of the immunogen, the first in complete, and the second, one week later, in Freunds incomplete adjuvant. After a further week had elapsed, a final 10 ug of protein of the immunogen in normal saline was administered intravenously and the mice sacrificed 3 days later.

Hybridoma Technology

Using sterile technique, the spleen from each mouse was removed, and a single cell suspension prepared by attrition of the tissue against a No. 3 stainless steel mesh (B. Fenenco and Co., Inc., Worcester Mass.). Splenocytes and cells from a nonsecretor mouse myeloma cell line (NS-1), were washed in RPMI-1640 medium, containing 2 mM L-glutamine, 1 mM sodium pyruvate, 100 U/ml penicillin, 100 ug/ml streptomycin, 0.25 ug/ml amphotericin B as fungizone, mixed at a 4:1 ratio, and fused by agitation in the presence of 50% polyethylene glycol 1430-1570 (BDH Chemical Co., Poole, England).

Thereafter, 96-well sterile tissue culture plates (Costar, Cambridge, Mass.) were seeded with the mixture at a density of 1 million cells in 100 ul per well. Hybridoma cells were selected out by growth in RPMI 1640 medium as above, supplemented with 15% fetal calf serum (heat inactivated), hypoxanthine, aminopterin, and thymidine (HAT selective medium Science 145, 709-10, 1964). Individual well supernatants were screened and selected cultures were cloned twice by limiting dilution. Dilutions are made and one quarter of the wells of a 96 tissue culture plate are seed with each of the following dilutions: 10, 5, 1, 0.5 cells/well. To sustain growth, thymocytes of 4 week old BALB/c mice were seeded in each well at a density of 1 million cells. Wells containing a resultant single colony of selected hybridoma cells lines were expanded, screened, and cloned a second time.

Solid Phase Radioimmuno and Enzyme-linked Immunosorbent Assay

The first screening assay utilized 50 ul of tissue culture supernatent (TCS) from each hybridoma well which was reacted with pooled adenomatous polyp extract in a radioimmunoassay (RIA). 5 ug protein of tissue extract was added to each well of a 96 well polyvinyl microtiter plate and allowed to dry in a 37° C. drying oven overnight. To block non-specific binding, 100 ul of 5% bovine serum albumen (BSA) in PBS containing calcium and magnesium, was incubated at 37° C. as were all subsequent incubations.

After washing the wells with 1% BSA in PBS, the hybridoma culture TCS was added as above and incubated for 1 hour. The plates were then washed 3 times to remove unbound immunoglobulin, and the wells incubated with $^{125}$I-labelled goat anti-mouse antibody at an activity of 75,000 cpm/25 ul/well. After a further hour's incubation, the plates were washed 3 times to remove unbound labelled antibody, and the plates subjected to autoradiography using Kodak XR film, and Dupont Lighting-Plus intensifying screens. After 16 hours at −70° C., the films were developed. In addition, individual well labelled antibody bound was detected by cutting the well from the plate and radioactive measurement in a gamma-counter. Negative controls wells contained NS-1 TCS.

The enzyme-linked immunosorbent assay (ELISA) according to Phillip and Lewis, Aust. N. Z. Journal of Surgery 48(5), 545-549, October 1978, was similarly performed, but used 5 ug protein/well of tissue or cell extract which was incubated for 24-48 hours at 4° C. before the hybridoma TCS (100 ul) was added. In this assay, 100 ul of goat anti-mouse IgG antibody conjugated to alkaline phosphatase (Sigma, St. Louis Mo.) was used to detect bound immunoglobulin, and a color reaction developed with p-nitrophenol phosphate 1 mg/ml (Sigma). The plate was read on an ELISA reader (Dynatech) at 1-3 hours. The results are expressed in O.D. (optical density)/5ug protein for tissue extracts.

The positive controls in this case were purified carcinoembryonic antigen (CEA) and their corresponding reactive monoclonal antibodies from various sources (COL-4, Laboratory of Tumor Immunology and Biology, NIH; IE-4, Dr. N. Epstein, Israel Institute for Biological Science, Ness Ziona, Israel; and organ specific neoantigen (OSN) (BAC 18.1, Dr. Z. Bentwich, Ben Ari Institute for Immunology, Rehovot, Israel), in Fink et al, Anticancer Research 6, 813-818, 1986.

Colonic Effluent Material

Material was collected from patients undergoing routine bowel preparation at George Washington University Medical School. The indications for colonoscopy were varied, but for 1.5 days, and on the day before the procedure, the subject took 1×250 ml bottle of magnesium citrate and 3 bisacodyl tablets. On the day of the procedure, a tap water enema was administered, the first clear return discarded and 100 ml of the last return evacuated, collected. This effluent was clarified at 1500 rpm in a clinical centrifuge for 10 minutes and filtered through a 0.8 u filter (Nalgene).

After the macroscopic and histologic outcome of the examination was known, effluent from 9 patients with colorectal cancer, 13 with adenomatous polyps, and 19 patients with macroscopically normal colonic mucosa were coded and evaluated in a standard ELISA as described above with the following modification. For each effluent sample, 5 ug of protein per well was incubated in 4 wells. 100ul of Adnab-9 TCS was used as primary monoclonal antibody in the first two wells, and PBS/RPMI 1640 was added to the last two. The ELISA is completed as above and the results obtained from the PBS/RPMI wells (effluent background) are subtracted from those obtained from the Adnab-9 containing wells. The final results are therefore derived from Adnab-9 bound-background/5 ug of each effluent tested.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A murine monoclonal antibody having all of the identifying characteristics of hybridoma ATCC HB10313 which
   (a) immunologically binds with extracts from human adenomatous colonic polyp tissue and does not immunologically bind with normal human liver or spleen tissue;
   (b) does not immunologically bind with colorectal cancer cell lines LS-174/T or HT-29;
   (c) does not immunologically bind with a colonic effluent sample from a subject with a macroscopically normal colonic mucosa as assessed by colonoscopy; and
   (d) does not immunologically bind with carcinoembryonic oncofetal antigen or ABO blood group substances.

2. The antibody of claim 1, wherein said antibody reacts and immunologically binds with extracts from pooled human tubular adenomatous colonic polyp tissue.

3. A hybridoma or a cell line derived therefrom having all of the identifying characteristics of ATCC HB10313 which is formed by fusion of non-immunoglobulin secreting myeloma cells and murine splenocytes, and which produces the murine monoclonal antibodies of claim 1, wherein said splenocytes are obtained from a mouse immunized with a membrane enriched fraction of human adenomatous colonic polyp tissue or an extract thereof.

4. The hybridoma or cell line of claim 3, wherein said splenocytes are obtained from a mouse immunized with a membrane enriched fraction of pooled human adenomatous colonic polyp tissue.

5. A method for producing monoclonal antibodies from hybridoma cultures comprising the steps of:
   (i) isolating murine splenocytes from a mouse immunized with a membrane enriched fraction of human adenomatous colonic polyp tissue;
   (ii) fusing said splenocytes with murine myeloma cells to form a hybridoma having all of the identifying characteristics of hybridoma ATCC HB10313;
   (iii) culturing said hybridoma cells in a culture medium to produce antibodies;
   (iv) screening said produced antibodies and isolating antibodies which:
      (a) immunologically bind with extracts from human adenomatous polyp tissue, but not normal human liver nor spleen tissue;
      (b) do not immunologically react to human colorectal cancer cell lines LS-174/T or HT-29;
      (c) do not substantially immunologically bind with a screening extract of human colorectal cancer tissue, normal human colorectal mucosa, ABO human blood group antigens, or carcinoembryonic oncofetal antigen;
   (v) selecting and cloning hybridomas having all of the identifying characteristics or hybridoma HTCC HB 10313.

6. The method of claim 5 where said adenomatous tissue is pooled tubular, tubulovillous or villous adenomatous colonic polyp tissue or an extract thereof.

7. The method of claim 5, wherein said screening extract is a pooled red blood cell membrane enriched extract.

8. The method of claim 5, wherein said screening extract is aqueous colorectal effluent from a human with a normal colonoscopic examination.

9. The method of claim 5, wherein said human adenomatous colonic polyp tissue is pooled tubular adenomatous colonic polyp tissue.

10. A method for producing monoclonal antibodies, which antibodies have the following immunological binding characteristics:

(a) immunologically binds with extracts from human adenomatous colonic polyp tissue and not with normal human liver nor spleen tissue;
(b) do not immunologically bind with colorectal cancer cell lines LS-174/T or HT-29;
(c) do not immunologically bind with a colonic effluent sample from a patient with a macroscopically normal colonic mucosa as assessed by colonoscopy;
(d) do not immunologically bind with carcinoembryonic oncofetal antigen nor ABO blood group substances, said method comprising the steps of:
(1) immunizing mice with membrane enriched fractions from pooled tubular adenomatous colonic polyps;
(2) removing the spleens from said mice and making a suspension of splenocytes;
(3) fusing said splenocytes with cells of a non-secreting murine myeloma cell line in the presence of a fusion inducing agent;
(4) culturing the fusing cells in wells containing a medium which will only support the growth of the fused cells;
(5) screening said fused cells for the production of antibodies having said immunological binding characteristics
(6) selecting and double cloning hybridomas having all of the identifying characteristics of hybridoma ATCC HB10313 and producing antibodies having said immunological binding characteristics; and
(7) recovering said antibodies from said clones.

* * * * *